United States Patent
Wong et al.

(10) Patent No.: US 7,018,990 B2
(45) Date of Patent: Mar. 28, 2006

(54) COMBINATION OF A FACTOR XA INHIBITOR AND CLOPIDOGREL

(75) Inventors: Pancras C. Wong, Plainsboro, NJ (US); Robert M. Knabb, Avondale, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/939,767

(22) Filed: Sep. 13, 2004

(65) Prior Publication Data

US 2005/0043382 A1    Feb. 24, 2005

Related U.S. Application Data

(63) Continuation of application No. 10/671,285, filed on Sep. 25, 2003, now abandoned.

(60) Provisional application No. 60/415,372, filed on Oct. 2, 2002.

(51) Int. Cl.
*A61K 31/60* (2006.01)
*A61K 31/44* (2006.01)
*A61K 31/42* (2006.01)
*A61K 31/22* (2006.01)

(52) U.S. Cl. ............... 514/161; 514/301; 514/379; 514/546

(58) Field of Classification Search ............ 514/161, 514/301, 379, 546
See application file for complete search history.

(56) References Cited

U.S. PATENT DOCUMENTS

| 4,529,596 | A | 7/1985 | Aubert et al. |
|---|---|---|---|
| 4,847,265 | A | 7/1989 | Badorc et al. |
| 5,576,328 | A | 11/1996 | Herbert et al. |
| 5,989,578 | A * | 11/1999 | Bernat et al. ............ 424/422 |
| 6,339,099 | B1 | 1/2002 | Lam et al. |
| 6,429,210 | B1 | 8/2002 | Bousquet et al. |
| 6,541,639 | B1 | 4/2003 | Zhou et al. |
| 6,667,332 | B1 | 12/2003 | Li et al. |
| 6,747,158 | B1 | 6/2004 | Li et al. |
| 2002/0025963 | A1 | 2/2002 | Lam et al. |
| 2003/0069258 | A1 | 4/2003 | Lam et al. |
| 2003/0144287 | A1 * | 7/2003 | Quan ............... 514/233.8 |
| 2004/0063772 | A1 | 4/2004 | Quan et al. |
| 2004/0198787 | A1 | 10/2004 | Li et al. |

FOREIGN PATENT DOCUMENTS

| WO | WO 98/56365 | 12/1998 |
|---|---|---|
| WO | WO 98/57951 | 12/1998 |
| WO | WO 02/08199 | 1/2002 |
| WO | WO 02/24690 | 3/2002 |

OTHER PUBLICATIONS

Cecil, Textbook of Medicine, 21st Edition, vol. 1, published 2000 by W.B. Saunders Company (PA), pp 291-296 and 1021-1028.*

* cited by examiner

*Primary Examiner*—Raymond J Henley, III
(74) *Attorney, Agent, or Firm*—Jing G. Sun; David H. Vance (57) ABSTRACT

The present application describes methods of using a combination of 1-(3'-aminobenzisoxazol-5'-yl)-3-trifluoromethyl-5-[[4-[(2'-dimethylaminomethyl)imidazol-1'-yl]-2-fluorophenyl]aminocarbonyl]pyrazole-hydrochloric acid salt, a factor Xa inhibitor, and Clopidogrel as anticoagulant agents for treatment of thromboembolic disorders and pharmaceutical compositions containing the same.

20 Claims, 4 Drawing Sheets

Fig. 1. Effects of vehicle, Compound A, clopidogrel, and the combination of Compound A and clopidogrel on clot inhibition, carotid blood flow (CBF), and bleeding time (BT) in rabbits. Means ± S.E. and n = 6 per group.

Fig. 2. Effects of vehicle, aspirin at 0.3 mg/kg/h, clopidogrel at 1 mg/kg/h, and the combination of aspirin at 0.3 mg/kg/h and clopidogrel at 1 mg/kg/h on clot inhibition, carotid blood flow (CBF), and bleeding time (BT) in rabbits. Means ± S.E. and n = 6 per group.

Fig. 3. Effects of vehicle, aspirin, Compound A and the combination of aspirin and Compound A on clot inhibition, carotid blood flow (CBF), and bleeding time (BT) in rabbits. Means ± S.E. and n = 6 per group.

Fig. 4. Effects of vehicle; aspirin; the combination of Compound A and clopidogrel; and, the combination of aspirin, clopidogrel, and Compound A on clot inhibition, carotid blood flow (CBF), and bleeding time (BT) in rabbits. Means ± S.E. and n = 6 per group.

COMBINATION OF A FACTOR XA INHIBITOR AND CLOPIDOGREL

CROSS-REFERENCE TO RELATED APPLICATIONS

This application is a continuation application of patent application U.S. Ser. No. 10/671,285, now abandoned filed Sep. 25, 2003, which claims the priority benefit of U.S. Provisional Application No. 60/415,372, filed Oct. 2, 2002, all of which are expressly incorporated fully herein by reference.

FIELD OF THE INVENTION

This invention relates generally to methods of using a combination of a factor Xa inhibitor and Clopidogrel as anticoagulant agents for treatment of thromboembolic disorders and pharmaceutical compositions containing the same.

BACKGROUND OF THE INVENTION

Compound A, 1-(3'-aminobenzisoxazol-5'-yl)-3-trifluoromethyl-5-[[4-[(2'-dimethylaminomethyl)imidazol-1'-yl]-2fluorophenyl]aminocarbonyl]pyrazole-hydrochloric acid salt, shown below:

Compound A is a factor Xa inhibitor and is currently being investigated as a potential drug candidate. WO98/57951, WO02/08199, and WO02/24690 describe the synthesis of 1-(3'-aminobenzisoxazol-5'-yl)-3-trifluoromethyl-5-[[4-[(2'-dimethylaminomethyl)imidazol-1'-yl]-2-fluorophenyl]aminocarbonyl]pyrazole, the contents of which are incorporated herein by reference.

Clopidogrel, an ADP receptor antagonist, is currently being marketed as Plavix® by Bristol-Myers Squibb Company and Sanofi-Synthelabo. Its structure and use are described in U.S. Pat. Nos. 4,529,596, 4,847,265, 5,576,328, and 6,429,210, the contents of which are incorporated herein by reference.

It is desirable to find combinations of agents for the treatment of thromboembolic disorders with enhanced efficacy and lower bleeding times. It is also desirable to find combinations of agents that allow for lower (i.e., sub-therapeutic and/or synergistic) dosages of each individual agent used in the combination.

SUMMARY OF THE INVENTION

Accordingly, the present invention provides a novel method for treating thromboembolic disorders, comprising: administering, to a host in need of such treatment, a combination of a therapeutically effective amount of Compound A and Clopidogrel or pharmaceutically acceptable salt or prodrug forms thereof.

The present invention provides a novel method of treating a patient in need of thromboembolic disorder treatment, comprising: administering a combination of Compound A and Clopidogrel or pharmaceutically acceptable salt or prodrug forms thereof in an amount effective to treat a thromboembolic disorder.

The present invention provides a novel method, comprising: administering a combination of Compound A and Clopidogrel or pharmaceutically acceptable salt or prodrug forms thereof in an amount effective to treat a thromboembolic disorder.

The present invention provides a novel pharmaceutical composition, comprising: a pharmaceutically acceptable carrier and a therapeutically effective amount of Compound A and Clopidogrel or pharmaceutically acceptable salt or prodrug forms thereof.

The present invention provides a novel combination of Compound A and Clopidogrel for use in therapy.

The present invention provides the use of a novel combination of Compound A and Clopidogrel for the manufacture of a medicament for the treatment of a thromboembolic disorder.

These and other objects, which will become apparent during the following detailed description, have been achieved by the inventors' discovery that a combination of Compound A and Clopidogrel provides enhanced efficacy without an increase in bleeding risk.

BRIEF DESCRIPTION OF THE DRAWINGS

The invention is illustrated by reference to the accompanying drawings described below.

DETAILED DESCRIPTION OF PREFERRED EMBODIMENTS

[1] Thus, in an embodiment, the present invention provides a novel method for treating a thromboembolic disorder, comprising: administering, to a host in need of such treatment, a therapeutically effective amount of:

(a) a first therapeutic agent which is 1-(3'-aminobenzisoxazol-5'-yl)-3-trifluoromethyl-5-[[4-[(2'-dimethylaminomethyl)imidazol-1'-yl]-2'-fluorphenyl]aminocarbonyl]pyrazole-hydrochloric acid salt (Compound A) or a pharmaceutically acceptable salt form thereof; and, (b) a second therapeutic agent which is Clopidogrel or a pharmaceutically acceptable salt form thereof.

[2] In a preferred embodiment, at least one of the first and second therapeutic agents is administered in a sub-therapeutic dosage.

[3] In another preferred embodiment, both the first and second therapeutic agents are administered in sub-therapeutic dosages.

[4] In another preferred embodiment, the first and second therapeutic agents are administered simultaneously.

[5] In another preferred embodiment, the first and second therapeutic agents are administered sequentially.

[6] In another preferred embodiment, the present invention provides a novel method for treating a thromboembolic disorder, further comprising: administering, to a host in need of such treatment, a therapeutically effective amount of:
(c) a third therapeutic agent selected from other anti-coagulant or coagulation inhibitory agents, anti-platelet or platelet inhibitory agents, thrombin inhibitors, thrombolytic agents, fibrinolytic agents, anti-arrythmic agents, and cholesterol/lipid lowering agents.

[7] In another preferred embodiment, the third therapeutic agent is selected from aspirin and pravastatin.

[8] In another preferred embodiment, the third therapeutic agent is aspirin.

[9] In another preferred embodiment, the third therapeutic agent is administered simultaneously with the first and second therapeutic agents.

[10] In another preferred embodiment, the third therapeutic agent is administered in a sub-therapeutic dosage.

[11] In another preferred embodiment, the thromboembolic disorder is selected from an arterial cardiovascular thromboembolic disorder, a venous cardiovascular thromboembolic disorder, an arterial cerebrovascular thromboembolic disorder, and a venous cerebrovascular thromboembolic disorder.

[12] In another preferred embodiment, the thromboembolic disorder is selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

[13] In another preferred embodiment, the thromboembolic disorder is selected from unstable angina, first myocardial infarction, recurrent myocardial infarction, ischemic sudden death, transient ischemic attack, and stroke.

[14] In another embodiment, the present invention provides a novel pharmaceutical composition, comprising:
(a) a first therapeutic agent which is 1-(3'-aminobenzisox-azol-5'-yl)-3-trifluoromethyl-5-[[4-[(2'-dimethylami-nomethyl)imidazol1'-yl]-2-fluorophenyl]aminocarbo-nyl]pyrazole-hydrochloric acid salt (Compound A) or a pharmaceutically acceptable salt form thereof;
(b) a second therapeutic agent which is Clopidogrel or a pharmaceutically acceptable salt form thereof; and,
(c) a pharmaceutically acceptable carrier.

[15] In another preferred embodiment, at least one of the first and second therapeutic agents is present in a sub-therapeutic dosage.

[16] In another preferred embodiment, both the first and second therapeutic agents are present in sub-therapeutic dosages.

[17] In another preferred embodiment, the present invention provides a novel pharmaceutical composition, further comprising:
(d) a third therapeutic agent selected from other anti-coagulant or coagulation inhibitory agents, anti-platelet or platelet inhibitory agents, thrombin inhibitors, thrombolytic agents, fibrinolytic agents, anti-arrythmic agents, and cholesterol/lipid lowering agents.

[18] In another preferred embodiment, the third therapeutic agent is selected from aspirin and pravastatin.

[19] In another preferred embodiment, the third therapeutic agent is aspirin.

[20] In a preferred embodiment, the third therapeutic agent is present in a sub-therapeutic dosage.

In another embodiment, the present invention provides a novel article of manufacture, comprising:
(a) a first container;
(b) a pharmaceutical composition located within the first container, wherein the composition is as defined above; and,
(c) a package insert stating that the pharmaceutical composition can be used for the treatment of a thromboembolic disorder.

In another preferred embodiment, the present invention provides a novel article of manufacture, further comprising:
(d) a second container; wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition is as defined above; and,
(c) a package insert stating that the pharmaceutical composition can be used in combination with a third therapeutic agent to treat a thromboembolic disorder.

In another preferred embodiment, the present invention provides a novel article of manufacture, further comprising:
(d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINTIONS

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it, this also includes reducing the risk of disease-state occurring or reoccurring; (b) inhibiting the disease-state, i.e., arresting it development; and/or (c) relieving the disease-state, i.e., causing regression of the disease state.

"Therapeutically effective amount" is intended to mean an amount of agents (a) and (b) of the present invention that is effective when administered in combination to treat a desired disease or condition. The combination of agents (a) and (b) is preferably a synergistic combination. Synergy, as described, for example, by Chou and Talalay, *Adv. Enzyme Regul.* 1984, 22:27–55, occurs when the effect of the compounds when administered in combination is greater than the additive effect of the compounds when administered alone as a single agent. In general, a synergistic effect is most clearly demonstrated at sub-optimal concentrations of the compounds (i.e., sub-therapeutic). Synergy can be in terms of lower cytotoxicity, increased antithrombotic effect, or some other beneficial effect of the combination compared with the individual components.

UTILITY

Compound A of this invention is an inhibitor of factor Xa and is useful as anticoagulant for the treatment or prevention of thromboembolic disorders in mammals (i.e., factor Xa-associated disorders). In general, a thromboembolic disorder is a circulatory disease caused by blood clots (i.e., diseases involving platelet activation and/or platelet aggregation). The term "thromboembolic disorders" as used herein includes arterial cardiovascular thromboembolic disorders, venous cardiovascular thromboembolic disorders, arterial cerebrovascular thromboembolic disorders, and venous cerebrovascular thromboembolic disorders. The term "thromboembolic disorders" as used herein includes specific disorders selected from, but not limited to, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty). The anticoagulant effect of Compound A of the present invention is believed to be due to inhibition of factor Xa or thrombin.

Administration of the first and second therapeutic agents preferably affords an efficacy advantage over the agents alone (i.e., a synergistic combination), preferably while permitting the use of lower doses of each (i.e., sub-therapeutic dosages). Administration of the first, second, and third therapeutic agents, preferably affords an efficacy advantage over the agents alone (i.e., a synergistic combination), preferably while permitting the use of lower doses of each (i.e., sub-therapeutic dosages). A lower dosage minimizes the potential of side effects, thereby providing an increased margin of safety. It is preferred that at least one of the first and second therapeutic agents is administered in a sub-therapeutic dose. It is also preferred that both the first and second therapeutic agents be administered in sub-therapeutic dosages. It is even more preferred that the first, second, and third therapeutic agents be administered in sub-therapeutic dosages. As noted previously, sub-therapeutic is intended to mean an amount of a therapeutic agent that by itself does not give the desired therapeutic effect for the disease being treated. Synergistic combination is intended to mean that the observed effect of the combination is greater than the sum of the individual agents administered alone.

The first and second agents may be administered at the same time or sequentially in any order at different points in time. Thus, each agent may be administered separately but sufficiently closely in time so as to provide the desired therapeutic effect. The first and second agents may also be formulated into a single pharmaceutical composition. The first, second, and third agents may also be administered at the same time or sequentially in any order at different points in time. The first, second, and third agents may also be formulated into a single pharmaceutical composition.

The therapeutic agents of the present invention are administered to a host in need thereof or are present in a pharmaceutical composition in a therapeutically effective amount. By "therapeutically effective amount" it is meant that appropriate amounts of the agents, when administered together or in combination with a third therapeutic agent, are effective to treat a thromboembolic disorder.

Additional therapeutic agents include other anti-coagulant or coagulation inhibitory agents, anti-platelet or platelet inhibitory agents, thrombin inhibitors, thrombolytic agents, fibrinolytic agents, anti-arrythmic agents, and cholesterol/lipid lowering agents.

Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatroban as well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion, or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine, and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide, and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, NK-104 (a.k.a. itavastatin, or nisvastatin or nisbastatin), and ZD-4522 (a.k.a. rosuvastatin, atavastatin, or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: the two compounds of the present invention or pharmaceutically acceptable salt forms thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a third therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and to protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* Mack Publishing Company, a standard reference text in this field.

These as well as other ways of minimizing contact between the components of combination products of the present invention, whether administered in a single dosage form or administered in separate forms but at the same time by the same manner, will be readily apparent to those skilled in the art, once armed with the present disclosure.

EXAMPLES

Example 1

Combination of Compound A and Clopidogrel

Rabbits were anesthetized with ketamine (50 mg/kg i.m.) and xylazine (10 mg/kg i.m.) and then surgically prepared with arterial and venous catheters. An electromagnetic flow probe was placed on a segment of an isolated carotid artery to monitor blood flow. Thrombus formation was induced by electrical stimulation of the carotid artery for 3 min at 4 mA using an external stainless-steel bipolar electrode. Carotid blood flow was measured continuously over a 45-min period to monitor thrombus occlusion. Compound A was infused intravenously whereas clopidogrel was infused into the portal vein. Both agents were infused 1 hour prior to the electrical stimulation of the carotid artery and continuously during the 45-min period.

The bleeding time effects of Compound A, clopidogrel, and their combination were examined in anesthetized rabbits. Rabbits were anesthetized as described above and their hind paws were shaved. A standard cut was made at the apex of the cuticle with a razor blade. Blood was allowed to flow freely by keeping the bleeding site in contact with 37° C. warm lactated Ringer's solution. Bleeding time was defined as the time after transection when bleeding was ceased. It was measured by averaging the bleeding time of three nail cuticles in the control and treatment period. Percentage change in cuticle bleeding time is calculated by comparing the bleeding time taken in the treatment period to the control bleeding time. Compounds were infused as described above.

Figure 1:
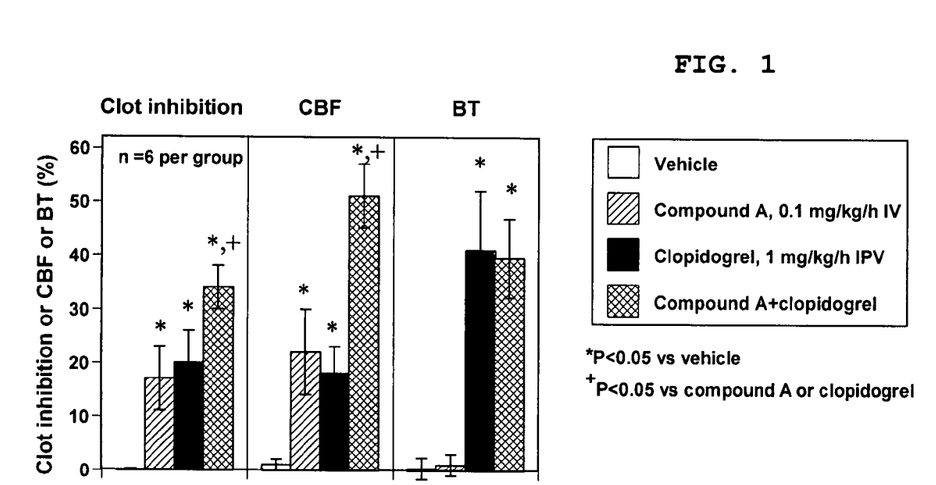
FIG. 1 shows the effects of vehicle, Compound A, clopidogrel, and the combination of Compound A and clopidogrel on clot inhibition, carotid blood flow (CBF), and bleeding time (BT) in rabbits.

As shown in FIG. 1, Compound A at 0.1 mg/kg/hr and clopidogrel at 1 mg/kg/hr produced moderate antithrombotic effects (i.e., moderate inhibition of clot formation and increase in carotid blood flow). At these low doses, compared to the vehicle-group, Compound A did not increase the bleeding time whereas clopidogrel increased the bleeding time significantly. Surprisingly, the combination of low doses of Compound A and clopidogrel produced a significant greater antithrombotic effect than either agent alone, but this combination did not cause a greater increase in bleeding time than clopidogrel alone (i.e., similar bleeding risk as clopidogrel in rabbits).

Example 2

Combination of Aspirin and Clopidogrel

The same experimental protocol as described in Example 1 was used in this study. Aspirin was infused intravenously whereas clopidogrel was infused into the portal vein. Both agents were infused 1 hour prior to the electrical stimulation of the carotid artery and the cuticle transection, and continuously to the end of the experiment.

Figure 2:
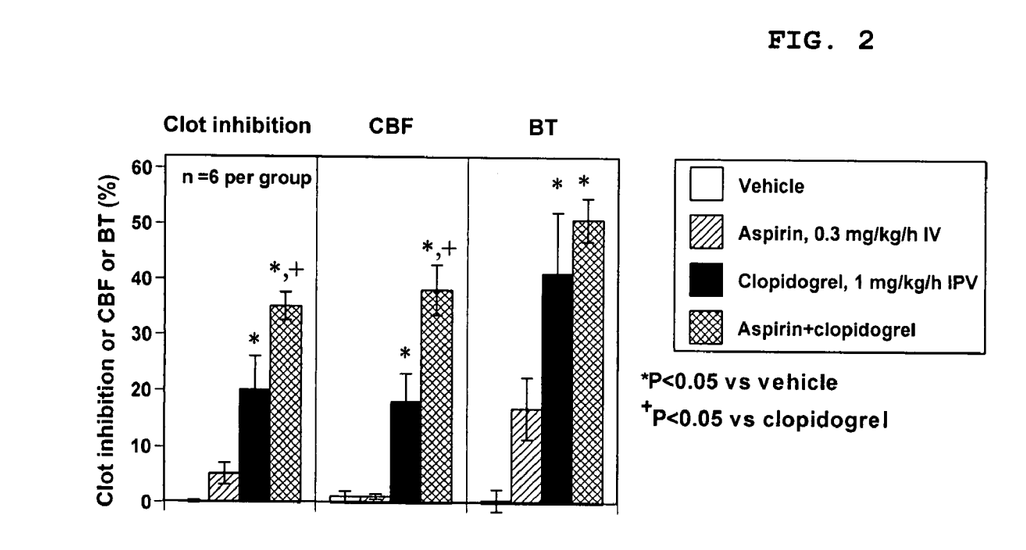
FIG. 2 shows the effects of vehicle, aspirin, clopidogrel, and the combination of aspirin and clopidogrel on clot inhibition, CBF, and BT in rabbits.

As shown in FIG. 2, aspirin at 0.3 mg/kg/hr was not effective in inhibiting the formation of clot and increasing carotid blood flow. Clopidogrel at 1 mg/kg/hr produced a moderate inhibition of clot formation and an increase in carotid blood flow. At these low doses, compared to the vehicle-group, aspirin did not increase the bleeding time significantly whereas clopidogrel increased the bleeding time significantly. Surprisingly, the combination of an ineffective dose of aspirin and a low dose of clopidogrel produced a significant greater antithrombotic effect than clopidogrel alone but this combination did not cause a greater increase in bleeding time than clopidogrel alone.

Example 3

The Combination of Compound A and Aspirin

Figure 3:
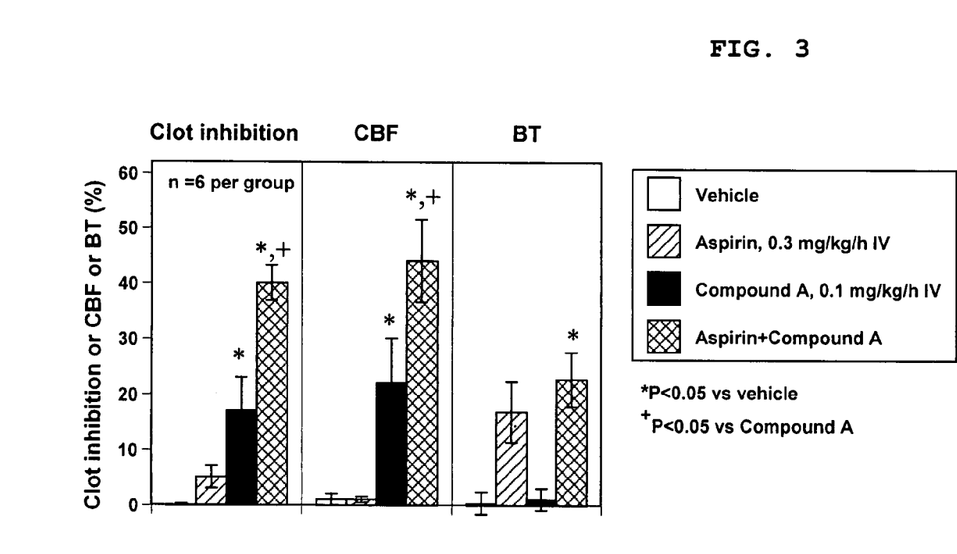
FIG. 3 shows the effects of vehicle, aspirin, Compound A and the combination of aspirin and Compound A on clot inhibition, CBF, and BT in rabbits.

The same experimental protocol as described in Example 1 was used in this study. Aspirin and Compound A were infused intravenously. As shown in FIG. 3, aspirin at 0.3 mg/kg/hr was not effective in inhibiting the formation of clot and increasing carotid blood flow. Compound A at 0.1 mg/kg/hr produced a moderate inhibition of clot formation and an increase in carotid blood flow. At these low doses, compared to the vehicle-group, aspirin and Compound A did not increase the bleeding time significantly. Surprisingly, the combination of an ineffective dose of aspirin and a low dose of Compound A produced a significant greater antithrombotic effect than Compound A alone but this combination had a bleeding risk like that of aspirin.

Example 4

The Combination of Aspirin, Compound A, and Clopidogrel

Figure 4:
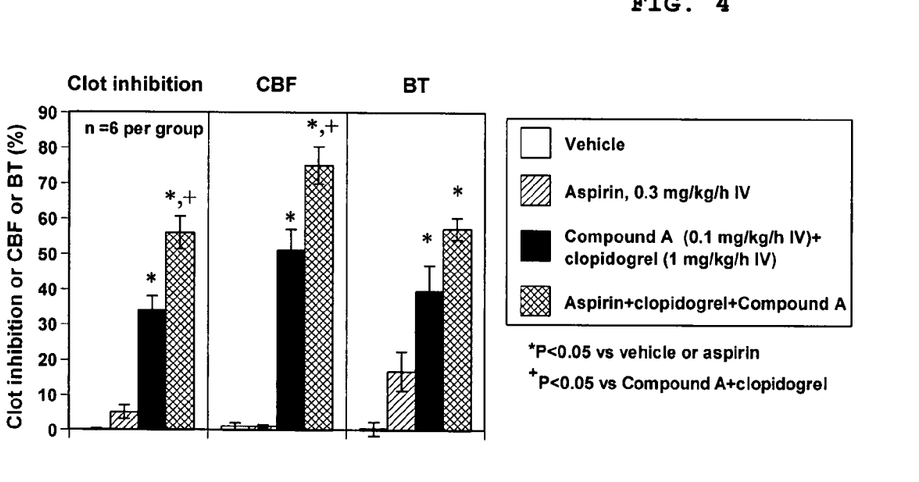
FIG. 4 shows the effects of vehicle; aspirin; the combination of Compound A and clopidogrel; and, the combination of aspirin, clopidogrel, and Compound A on clot inhibition, CBF, and BT in rabbits.

The same experimental protocol as described in Examples 1 to 3 was used in this study. As shown in FIG. 4, aspirin at 0.3 mg/kg/hr was not effective in inhibiting the formation of clot and increasing carotid blood flow. The combination of Compound A at 0.1 mg/kg/hr and clopidogrel at 1 mg/kg/hr produced a significant inhibition of clot formation and an increase in carotid blood flow. At these doses, compared to the vehicle-group, the combination of Compound A and clopidogrel but not aspirin increased the bleeding time significantly. Surprisingly, the combination of an ineffective dose of aspirin and a low dose of Compound A produced a significant greater antithrombotic effect than the combination of Compound A and clopidogrel, but the combination of aspirin, clopidogrel and Compound A did not cause a greater increase in bleeding time than the combination of Compound A and clopidogrel. These results show that aspirin at an ineffective dose enhanced the antithrombotic effect of the combination of low doses of clopidogrel and Compound A and did not increase the bleeding effect of the combination of clopidogrel and Compound A in rabbits.

Numerous modifications and variations of the present invention are possible in light of the above teachings. It is therefore to be understood that within the scope of the appended claims, the invention may be practiced otherwise that as specifically described herein.

What is claimed is:

1. A method for treating a thromboembolic disorder, comprising: administering, to a host in need of such treatment, a therapeutically effective amount of:
   (a) a first therapeutic agent which is 1-(3'-aminobenzisoxazol-5'-yl)-3-trifluoromethyl-5-[[4-[(2'-dimethylaminomethyl)imidazol-1'-yl]-2-fluorophenyl]aminocarbonyl]pyrazole-hydrochloric acid salt (Compound A) or a pharmaceutically acceptable salt form thereof; and,
   (b) a second therapeutic agent which is Clopidogrel or a pharmaceutically acceptable salt form thereof; wherein said first and second agents are administered in therapeutically effective amounts which provide a synergistic antithrombotic effect.

2. A method according to claim 1, wherein at least one of the first and second therapeutic agents is administered in a sub-therapeutic dosage.

3. A method according to claim 2, wherein both the first and second therapeutic agents are administered in sub-therapeutic dosages.

4. A method according to claim 1, wherein the first and second therapeutic agents are administered simultaneously.

5. A method according to claim 1, wherein the first and second therapeutic agents are administered sequentially.

6. A method according to claim 1, wherein the method further comprises: administering, to a host in need of such treatment, a therapeutically effective amount of:
   (c) a third therapeutic agent selected from other anticoagulant or coagulation inhibitory agents, anti-platelet or platelet inhibitory agents, thrombin inhibitors, thrombolytic agents, fibrinolytic agents, anti-arrythmic agents, and cholesterol/lipid lowering agents.

7. A method according to claim 6, wherein the third therapeutic agent is selected from aspirin and pravastatin.

8. A method according to claim 7, wherein the third therapeutic agent is aspirin.

9. A method according to claim 6, wherein the third therapeutic agent is administered simultaneously with the first and second therapeutic agents.

10. A method according to claim 6, wherein the third therapeutic agent is administered in a sub-therapeutic dosage.

11. A method according to claim 1, wherein the thromboembolic disorder is selected from an arterial cardiovascular thromboembolic disorder, a venous cardiovascular thromboembolic disorder, an arterial cerebrovascular thromboembolic disorder, and a venous cerebrovascular thromboembolic disorder.

12. A method according to claim 11, wherein the thromboembolic disorder is selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

13. A method according to claim 12, wherein the thromboembolic disorder is selected from unstable angina, first myocardial infarction, recurrent myocardial infarction, ischemic sudden death, transient ischemic attack, and stroke.

14. A pharmaceutical composition, comprising:
   (a) a first therapeutic agent which is 1-(3'-aminobenzisoxazol-5'-yl)-3-trifluoromethyl-5-[[4-[(2'-dimethylaminomethyl)imidazol-1'-yl]-2-fluorophenyl]aminocarbonyl]pyrazole-hydrochloric acid salt (Compound A) or a pharmaceutically acceptable salt form thereof;
   (b) a second therapeutic agent which is Clopidogrel or a pharmaceutically acceptable salt form thereof; and,
   (c) a pharmaceutically acceptable carrier; wherein said first and second therapeutic agents are present in amounts which provide a synergistic antithrombotic effect upon administration.

15. A pharmaceutical composition according to claim 14, wherein at least one of the first and second therapeutic agents is present in a sub-therapeutic dosage.

16. A pharmaceutical composition according to claim 15, wherein both the first and second therapeutic agents are present in sub-therapeutic dosages.

17. A pharmaceutical composition according to claim 14, further comprising:
   (d) a third therapeutic agent selected from other anticoagulant or coagulation inhibitory agents, anti-platelet or platelet inhibitory agents, thrombin inhibitors, thrombolytic agents, fibrinolytic agents, anti-arrythmic agents, and cholesterol/lipid lowering agents.

18. A pharmaceutical composition according to claim 17, wherein the third therapeutic agent is selected from aspirin and pravastatin.

19. A pharmaceutical composition according to claim 18, wherein the third therapeutic agent is aspirin.

20. A pharmaceutical composition according to claim 17, wherein the third therapeutic agent is present in a sub-therapeutic dosage.

* * * * *